(12) United States Patent
Jung et al.

(10) Patent No.: US 8,936,848 B2
(45) Date of Patent: Jan. 20, 2015

(54) NON-PRE-COLORED MULTI-LAYER ZIRCONIA DENTAL BLANK THAT HAS A GRADUAL CHANGE IN TRANSLUCENCY THROUGH A THICKNESS AFTER SINTERING

(75) Inventors: Yunoh Jung, Murray, UT (US); Daniel Yonil Jung, Murray, UT (US); Young Jin Kim, West Valley City, UT (US); Yoonho Jun, West Valley City, UT (US)

(73) Assignee: B&D Dental Corp, West Valley City, UT (US)

( * ) Notice: Subject to any disclaimer, the term of this patent is extended or adjusted under 35 U.S.C. 154(b) by 318 days.

(21) Appl. No.: 13/403,417

(22) Filed: Feb. 23, 2012

(65) Prior Publication Data

US 2013/0221554 A1   Aug. 29, 2013

(51) Int. Cl.
*A61C 13/00* (2006.01)
*C04B 35/48* (2006.01)
*B32B 18/00* (2006.01)
*C04B 35/486* (2006.01)

(52) U.S. Cl.
CPC ......... *A61C 13/0022* (2013.01); *C04B 2235/77* (2013.01); *B32B 18/00* (2013.01); *A61C 13/0004* (2013.01); *A61C 13/0006* (2013.01); *C04B 35/486* (2013.01); *C04B 2235/6567* (2013.01); *C04B 2235/3225* (2013.01); *C04B 2235/608* (2013.01); *C04B 2235/5445* (2013.01); *C04B 2235/612* (2013.01); *C04B 2235/96* (2013.01); *C04B 2235/9615* (2013.01); *C04B 2237/704* (2013.01); *C04B 2235/9653* (2013.01); *C04B 2237/348* (2013.01); *C04B 2235/9661* (2013.01); *C04B 2237/582* (2013.01)

USPC ........ 428/211.1; 428/215; 428/697; 428/701; 428/702; 501/134

(58) Field of Classification Search
None
See application file for complete search history.

(56) References Cited

U.S. PATENT DOCUMENTS

| | | |
|---|---|---|
| 6,354,836 B1 | 3/2002 | Panzera et al. |
| 7,011,522 B2 | 3/2006 | Panzera et al. |
| 7,090,721 B2 | 8/2006 | Craig et al. |
| 7,981,531 B2 | 7/2011 | Rheinberger et al. |
| 8,025,992 B2 | 9/2011 | Engels et al. |

(Continued)

FOREIGN PATENT DOCUMENTS

| | | |
|---|---|---|
| WO | WO 2011156602 A2 * | 12/2011 |
| WO | WO 2013/003990 | 1/2013 |
| WO | WO2014062375 A1 * | 4/2014 |

OTHER PUBLICATIONS

U.S. Appl. No. 13/403,494, filed Feb. 23, 2012, Yunoh Jung.

(Continued)

*Primary Examiner* — David Sample
(74) *Attorney, Agent, or Firm* — Thorpe North & Western LLP

(57) ABSTRACT

A dental block for producing a dental prosthesis comprises a green body including zirconia and having a chemical composition including increasing amounts of yttria through a thickness of the green body. The green body is substantially opaque with a substantially consistent optical characteristic of non-translucency with respect to visible light across the thickness, and is subsequently millable and sinterable to form the dental prosthesis with an optical characteristic of increasing translucency through a thickness of the dental prosthesis.

9 Claims, 11 Drawing Sheets

(56) References Cited

U.S. PATENT DOCUMENTS

| | | | |
|---|---|---|---|
| 2007/0292597 A1* | 12/2007 | Ritzberger et al. | 427/2.29 |
| 2008/0064011 A1* | 3/2008 | Rheinberger et al. | 433/215 |
| 2008/0274440 A1 | 11/2008 | Smith et al. | |
| 2008/0303181 A1* | 12/2008 | Holand et al. | 264/16 |
| 2009/0092531 A1 | 4/2009 | Katusic et al. | |
| 2010/0133711 A1 | 6/2010 | Brodkin et al. | |
| 2010/0209876 A1* | 8/2010 | Wagner et al. | 433/201.1 |
| 2010/0216095 A1* | 8/2010 | Scharf | 433/212.1 |
| 2011/0236855 A1 | 9/2011 | Rheinberger et al. | |
| 2011/0236860 A1* | 9/2011 | Jahns et al. | 433/222.1 |
| 2011/0319254 A1* | 12/2011 | Ritzberger et al. | 501/134 |
| 2012/0139141 A1* | 6/2012 | Khan et al. | 264/20 |
| 2013/0115365 A1* | 5/2013 | Wang et al. | 427/2.29 |
| 2013/0221554 A1 | 8/2013 | Jung et al. | |
| 2013/0231239 A1* | 9/2013 | Carden et al. | 501/134 |

OTHER PUBLICATIONS

Hongbo Guo et al.; Laminated and functionally graded hydroxyaptite/yttria stabilized tetragonal zirconia composites fabricated by spark plasma sintering; Biomaterials; 2003; pp. 667-675; vol. 24; Elsevier Science Ltd.

U.S. Appl. No. 13/403,494, filed Feb. 23, 2012, Yunoh Jung; office action dated Mar. 14, 2014.

Akira Hasegawa, "Color and Translucency of In Vivo Natural Central Incisors"; Apr. 2000, the journal of Prosthetic Dentistry, vol. 83; pp. 418-422.

John M. Powers, "Guide to All Ceramic Bonding"; Jun. 5, 2012; Kurarydental.com, pp. 1-12.

U.S. Appl. No. 13/403,494, filed Feb. 23, 2012, Yunoh Jung; office action dated Jun. 6, 2013.

* cited by examiner

| | | Total light Transmittance (at 600 nm) | |
|---|---|---|---|
| ——— | Layer E (Fifth layer) | 52.91 %T | Sample E (thickness 0.6mm) |
| —‥ | Layer D (Forth layer) | 51.55 %T | Sample D (thickness 0.6mm) |
| ----- | Layer C (Third layer) | 51.08 %T | Sample C (thickness 0.6mm) |
| —·— | Layer B (Second layer) | 50.92 %T | Sample B (thickness 0.6mm) |
| ········ | Layer A (First layer) | 49.72 %T | Sample A (thickness 0.6mm) |

NON-PRE-COLORED MULTI-LAYER ZIRCONIA DENTAL BLANK THAT HAS A GRADUAL CHANGE IN TRANSLUCENCY THROUGH A THICKNESS AFTER SINTERING

RELATED APPLICATION(S)

This is related to U.S. patent application Ser. No. 13/403,494, filed Feb. 23, 2012, entitled "Non-Pre-Colored Multi-Layer Zirconia Dental Blank that has a Gradual Change in Chroma through a Thickness After Sintering"; which is herein incorporated by reference.

BACKGROUND

1. Field of the Invention

The present invention relates generally to dental blanks for forming dental prostheses. More particularly, the present invention relates to a green body zirconia dental blank with a chemical compositions of increasing amounts of yttria through a thickness thereof and a pre-sintered optical characteristic of non-translucency with respect to visible light that is substantially consistent and opaque across the thickness; and being milled, colored and sintered to form the dental prosthesis with an optical characteristic of increasing translucency through a thickness of the dental prosthesis after sintering.

2. Related Art

There are three main classes of dental ceramics: Group I—predominantly glassy materials; Group II—particle-filled glasses and glass-ceramics as a special subset of particle-filled glasses; and Group III—polycrystalline ceramics.

Group I—predominantly glassy ceramics—are 3-D networks of atoms having no regular pattern to the spacing between nearest or next nearest neighbors, thus their structure is 'amorphous' or without form. Glasses in dental ceramics derive principally from a group of mined minerals called feldspar and are based on silica (silicon oxide) and alumina (aluminum oxide), hence feldspathic porcelains belong to a family called alumino-silicate glasses.

Group II—particle-filled glasses and glass-ceramics—have filler particles that are added to the base glass composition in order to improve mechanical properties and to control optical effects such as opalescence, color and opacity. These fillers are usually crystalline but can also be particles of a higher melting glass. Glass-ceramics in Group II have crystalline filler particles added mechanically to the glass, e.g. by simply mixing together crystalline and glass powders prior to firing. In a more recent approach, the filler particles are grown inside the glass object (prosthesis) after the object has been formed. After forming, the glass object is given a special heat treatment, causing the precipitation and growth of crystallites within the glass. Such particle-filled composites are called glass-ceramics. More recently a glass-ceramic containing 70 vol % crystalline lithium disilicate filler has been commercialized for dental use. Example of this is Empress 2, now e.maxPress and e.maxCAD from IvoClar-Vivadent.

Group III—polycrystalline ceramics—have no glassy components; all of the atoms are densely packed into regular arrays that are much more difficult to drive a crack through than atoms in the less dense and irregular network found in glasses. Hence, polycrystalline ceramics are generally much tougher and stronger than group I and II glassy ceramics. Polycrystalline ceramics are more difficult to process into complex shapes (e.g. a prosthesis) than are glassy ceramics and tend to be relatively opaque compared to glassy ceramics. (Ceramic materials in dentistry: historical evolution and current practice (2011), J R Kelly, University of Connecticut Health Center, Department of Reconstructive Sciences, Farminton, Conn.).

Advanced polycrystalline ceramic materials such as zirconia have great potential as substitutes for traditional materials in many biomedical applications. Since the end of the 1990s, the form of partially stabilized zirconia has been promoted as suitable for dental use due to its excellent strength and superior fracture resistance. In addition, zirconia bio-ceramic presents enhanced biocompatibility, low radioactivity, and good aesthetic properties. The introduction of computer-aided design/computer-aided manufacturing (CAD/CAM) techniques has increased the general acceptance of zirconia in dentistry.

Zirconium dioxide (ZrO2) known as zirconia, is a crystalline oxide of zirconium. Although pure zirconium oxide does not occur in nature, it is found in the minerals baddeleyite and zircon (ZrSiO4). At ordinary temperatures, it has a hexagonal close-packed crystalline structure and forms a number of compounds such as zirconate (ZrO3−2) and zirconyl (ZrO+2) salts. Zirconia is obtained as a powder and possesses both acidic and basic properties. Zirconium oxide crystals are arranged in crystalline cells (mesh) which can be categorized in three crystallographic phases: 1) the cubic (C) in the form of a straight prism with square sides 2) the tetragonal (T) in the form of a straight prism with rectangular sides and 3) the monoclinic (M) in the form of a deformed prism with parallelepiped sides. The cubic phase is stable above 2,370° C. and has moderate mechanical properties, the tetragonal phase is stable between 1,170° C. and 2,370° C. and allows a ceramic with improved mechanical properties to be obtained, while the monoclinic phase, which is stable at room temperatures up to 1,170° C., presents reduced mechanical performance and may contribute to a reduction in the cohesion of the ceramic particles and thus of the density.

Partially stabilized zirconia is a mixture of zirconia polymorphs, because insufficient cubic phase-forming oxide (stabilizer) has been added and a cubic plus metastable tetragonal ZrO2 mixture is obtained. A smaller addition of stabilizer to the pure zirconia will bring its structure into a tetragonal phase at a temperature higher than 1,000° C. and a mixture of cubic phase and monoclinic (or tetragonal) phase at a lower temperature. This partially stabilized zirconia is also called tetragonal zirconia polycrystal (TZP). Several different oxides, eg, magnesium oxide (MgO), yttrium oxide, (Y2O3), calcium oxide (CaO), and cerium oxide (Ce2O3), can be added to zirconia to stabilize the tetragonal and/or cubic phases.

Nowadays dental restorations or prostheses are often made using zirconia ceramic with CAD (Computer Aided Design) and CAM (Computer Aided Machining) process, which typically includes:
- capturing data representing the shape of a patient's teeth, for example by scanning a plaster model of the patient's teeth or alternatively by scanning the actual teeth in the patient's mouth;
- designing the shape of a dental restoration precursor based on the captured data using software, such as computer-aided design (CAD) software;
- machining the dental restoration precursor to correspond to the designed shape, for example, by an automated Computer Numerical Controlled (CNC) machine; and
- optionally finishing the dental restoration precursor by sintering and/or veneering.

A common method of making dental restorations includes milling a restoration precursor out of a zirconia disc/blank of a pre-sintered but still porous ceramic material. The disc/ blank is typically formed by compacting an amount of ceramic powder. The zirconia disc/blank of compacted powder is usually subsequently pre-sintered to provide it with the required mechanical stability for handling and machining. Once the restoration precursor has been obtained from machining the disc/blank the precursor is typically sintered in the further process of making the final dental restoration. During sintering the precursor typically shrinks, generally proportionally, because the initially porous material reduces in porosity and increases in density. For this reason the restoration precursor may be initially larger, for example about 18 to 27%, than the desired final shape after sintering, to account for shrinkage during the sintering step. To form the final dental restoration the sintered restoration precursor may be veneered or otherwise finished.

Some Group I or II glass ceramic blocks already have different upper and lower optical properties, such as translucency, brightness, reflectance and color. Thus, the glass ceramic block itself already has pre-determined optical properties. For example, see U.S. Pat. No. 8,025,992. Such a pre-colored glass ceramic block can be used primarily in dentists' office with a view to finish the indirect treatment with just one visit. The dental laboratory can also be a user. Here the indirect treatment mainly means to put a crown, bridge, inlay and/or onlay in replacement of the damaged tooth.

After the dentist preps the tooth, he/she chooses a glass ceramic block that already has color in it. Each layer of the block has a color profile already integrated into the block after the pre-sintered stage and it is implied that each layer should not be different in chemical characteristics. For each layer, coloring is affected only by addition of coloring oxides to the melt from which the granulate is obtained, or to the ground granulate and not due to differing chemical characteristics. These oxides are then present separately. In summary, these pre-colored, glass ceramic blocks already have predetermined, built-in optical properties in the block It can be advantageous for small, ready-to-be-used individual blocks to have these built-in optical characteristics for small production. But pre-colored individual blocks can also be disadvantageous for mass production of prostheses of various sizes and various desired optical characteristics.

The milling machine mills the pre-colored glass ceramic block one at a time in a single mill sequence. The inefficiency with this ceramic block is that if there are 15 different colors of prosthetic teeth to be milled, then the machine should be stopped each time so that the milled block could be removed and each different block could be loaded. Thus, the pre-colored glass ceramic blocks are not efficient for dental laboratories where numerous cases should be milled, regardless of the optical properties of the dental prostheses. These laboratories need to reduce the stopping of the machines as much as possible to save time and increase productivity.

For examples of pre-colored dental blocks, see U.S. Pat. Nos. 8,025,992 and 7,981,531; and US Patent Publication No. 2011-0236855. For examples of zirconia dental blocks, see U.S. Pat. Nos. 7,011,522 and 6,354,836.

SUMMARY OF THE INVENTION

It has been recognized that it would be advantageous to develop a dental prosthesis with improved or more natural optical characteristics, such as translucency and/or chroma, and/or with different layers having different optical characteristics. In addition, it has been recognized that it would be advantageous to develop a green body dental blank having different layers of different chemical compositions, but substantially consistent optical characteristics prior to sintering, and which can be milled, colored and sintered to obtain layers of different optical characteristics.

The invention provides a dental block for producing a dental prosthesis. The dental block comprises a green body comprising zirconia. The green body has multiple different layers, each having a different chemical composition between adjacent layers. The different chemical composition includes different amounts of yttria between the adjacent layers. The green body is substantially opaque with a substantially consistent optical characteristic of non-translucency with respect to visible light across the layers. The green body has a brightness/lightness $L^*$ value between 10 to 20 for a sample thickness of 1 to 1.3 mm in accordance with CIE $L^*a^*b^*$ colorimetric system. The green body is subsequently millable and sinterable to form the dental prosthesis with the multiple different layers having different optical characteristics of translucency.

In accordance with a more detailed aspect of the present invention, the amount of yttria can be increased incrementally from a lower layer to an upper layer. The amount of yttria can be increased incrementally from 4.5-6 wt % in the lower layer to 6-10 wt % in the upper layer. In addition, the multiple different layers can have different thicknesses with respect to one another with the lower layer having a thickness between 2-5 mm and the upper layer having a thickness between 0.5-2 mm. Furthermore, the green body can be without color pigment.

In addition, the invention provides a dental block for producing a dental prosthesis. The dental block comprises a green body comprising 60-99.9 wt % zirconia that is soft sintered or pre-sintered without color pigment. The green body has a different chemical composition through a thickness of the green body and being substantially opaque with a substantially consistent optical characteristic of non-translucency with respect to visible light throught the thickness. The different chemical composition includes increasing amounts of yttria through the thickness with a lower portion having 4.5-6 wt % yttria and an upper portion having 6-10 wt % yttria. The green body has a brightness/lightness $L^*$ value between 10 to 20 for a sample thickness of 1 to 1.3 mm in accordance with CIE $L^*a^*b^*$ colorimetric system. The green body is subsequently millable, colorable and sinterable to form the dental prosthesis with an optical characteristic of increasing translucency through a thickness of the dental prosthesis.

In accordance with a more detailed aspect of the present invention, the green body can be millable to form a green dental prosthesis that can be colorable and sinterable to form the dental prosthesis with the optical characteristic of increasing translucency through the thickness of the dental prosthesis after sintering. In addition, the green body can have multiple different layers with different thicknesses with respect to one another with a lower layer having a thickness between 2-5 mm and an upper layer having a thickness between 0.5-2 mm. Furthermore, the green body can have a continuous change in the amount of yttria through the thickness.

In addition, the invention provides a method for making a dental blank for use in producing a dental prosthesis, the method comprising:
 a) forming ziconia and yttria into a desired shape;
 b) increasing an amount of yttria through a thickness of the desired shape; and
 c) pre-sintering or soft sintering the desired shape to form a green body dental blank with a different chemical composition of the amount of yttria through the thickness and being substantially opaque with a substantially consistent optical characteristic of non-translucency with respect to visible light across the thickness, the green body dental blank having a brightness/lightness L* value between 10 to 20 for a sample thickness of 1 to 1.3 mm in accordance with CIE L*a*b* colorimetric system.

In accordance with a more detailed aspect of the present invention, the amount of yttria can be increased incrementally from 4.5-6 wt % in a lower portion to 6-10 wt % in an upper portion. In addition, forming zirconia and yttria into a desired shape and increasing the amount of yttria through a thickness of the desired shape can further comprise: a) combining zirconia with a first amount of yttria in a first mixture; b) forming the first mixture into a first layer; c) combining zirconia with a second different amount of yttria in at least a second mixture; and d) disposing the at least the second mixture into a second layer on the first layer. In addition, the amount of yttria can be increased incrementally from 4.5-6 wt % in a lower layer to 6-10 wt % in an upper layer. In addition, the layers can have different thicknesses with respect to one another with a lower layer having a thickness between 2-5 mm and an upper layer having a thickness between 0.5-2 mm. In addition, the pre-sintering can be done in the presence of atmospheric air. In addition, the zirconia and the yttria can be formed without color pigment. Furthermore, the method can include a) milling a green body dental prosthesis from the green body dental blank; b) coloring the green body dental prosthesis; and c) sintering the green body dental prosthesis to form the dental prosthesis with an optical characteristic of increasing translucency across a thickness of the dental prosthesis after sintering.

Furthermore, the invention provides a method for making a dental a dental prosthesis, the method comprising:

a) obtaining a green body dental blank including zirconia and having a chemical composition with increasing amounts of yttria through a thickness of the dental blank and being substantially opaque with a substantially consistent optical characteristic of non-translucency with respect to visible light across the thickness, the green body dental blank having a brightness/lightness L* value between 10 to 20 for a sample thickness of 1 to 1.3 mm in accordance with CIE L*a*b* colorimetric system;

b) milling a green body dental prosthesis from the dental blank;

c) coloring the green body dental prosthesis;

d) sintering the green body dental prosthesis to form the dental prosthesis having an optical characteristic of increasing translucency across the thickness of the dental prosthesis after sintering.

In accordance with a more detailed aspect of the present invention, the sintering can be done in the presence of atmospheric air.

Thus, the current invention introduces a method of producing a yttria (Y2O3) stabilized polycrystalline dental zirconia disc/blank that does not contain color pigments in it. Incremental addition of yttria (Y2O3) was applied towards one direction in the production of this disc/blank. After pre-sintering the green body looks generally opaque over the entire surface. The dental restoration would then be milled out of this green body, followed by coloring and final sintering. Only at this restoration stage can the desirable optical properties match that found in the human tooth.

By increasing the amount of yttria (Y2O3) towards the incisal area at the initial powder characterization stage before green body molding, it was discovered that the translucency level was increased and color chroma level was decreased after primary sintering which is a typical characteristic of a natural human tooth.

The benefit of this discovery of incremental addition of yttria (Y2O3) to one specific direction is that it enables the smooth transition of a certain level of translucency and color chroma to another level. Also, separating the processes of 1) producing a non-colored green body after the pre-sintering stage and 2) implementing custom coloring in a subsequent stage, enables the mass production of multiple dental restorations in dental laboratories.

The current invention zirconia material can be used to manufacture dental prostheses including, but not limited to, crowns, partial crowns, bridges, inlays, onlays, orthodontic appliances, space maintainers, tooth replacement appliances, splints, dentures, posts, facings, veneers, facets, implants, abutments, cylinders, and connectors.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
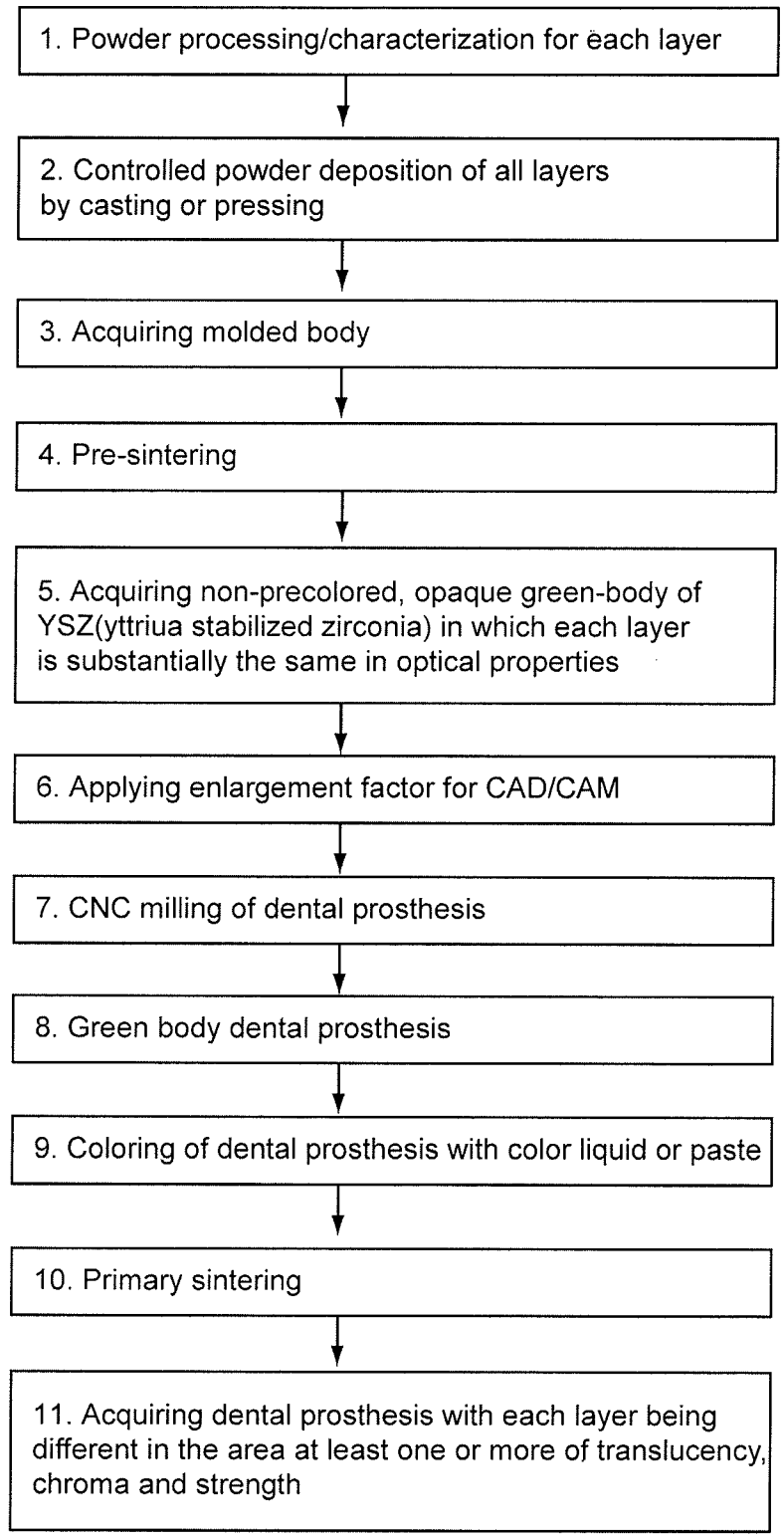
FIG. 1 is a flowchart showing a method of making a green body dental block and a dental prosthesis in accordance with an embodiment of the present invention.
Figure 2A:
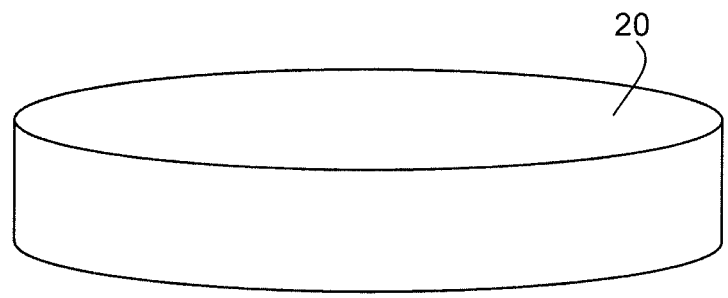
FIG. 2a is a perspective view of the green body dental block in accordance with an embodiment of the present invention.
Figure 2B:
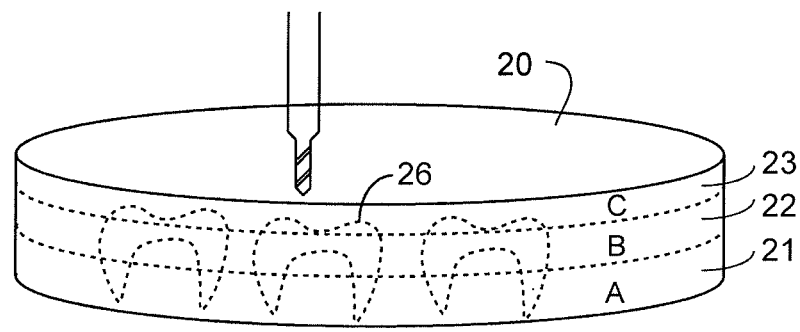
FIG. 2b is a schematic perspective view of the green body dental block of FIG. 1 shown with multiple different layers and a dental prosthesis to be milled therefrom.
Figure 2C:
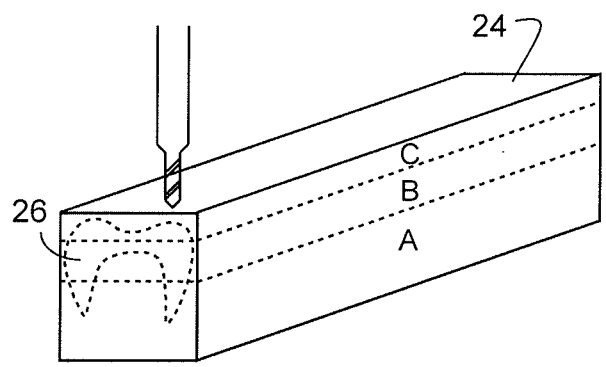
FIG. 2c is a schematic perspective view of another green body dental block in accordance with another embodiment of the present invention.
Figure 2D:
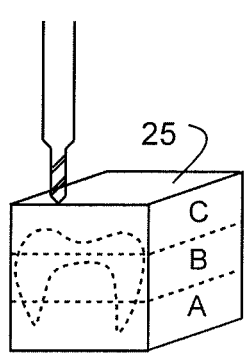
FIG. 2d is a schematic perspective view of another green body dental block in accordance with another embodiment of the present invention.
Figure 2E:
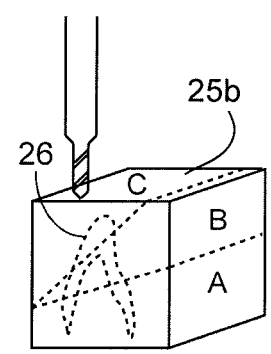
FIG. 2e is a schematic perspective view of another green body dental block in accordance with another embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The terms "zirconia green body" and "green body" are used interchangeably herein to mean a three-dimensional granular structure comprised of zirconia oxide particles, which is not sintered yet or, more frequently referred to, is partially sintered, pre-sintered or soft sintered at a temperature of 900-1100° C., to facilitate millability of the disc/blank. The terms "green body dental prosthesis" and "green dental prosthesis" are used interchangeably herein to mean a dental prosthesis that has been milled from the green body, but has not yet been sintered to become the final dental prosthesis.

The terms "pre-sintering" and "soft sintering" and "partial sintering" are used interchangeably herein to mean a reduction of size and/or number or the elimination of interparticle pores in a granular structure comprised of particles by heating, without melting, of the particles. Pre-sintering is carried out at a temperature of around 900-1100° C. to facilitate the machine milling of molded zirconia disc/blank. After pre-sintering zirconia is still porous and as a result becomes easy for color-ion liquid application. Pre-sintering or soft sintering is performed on the cast or molded zirconia to obtain a green body with sufficient strength to be milled.

The terms "sintering" and "primary sintering" and "final sintering" are used interchangeably herein. After the green body of the specific dental restoration (or green body dental prosthesis or green dental prosthesis) is ready from the milling, primary/final sintering is done at a much higher temperature (around 1300-1600° C.) than pre-sintering. After primary sintering, zirconia gets full densification, over 99%, and reaches its full flexural strength. Sintering is performed on the milled (and colored) green body dental prosthesis to obtain a dental prosthesis with final strength and optical characteristics, such as translucency and/or color intensity/chroma.

The term "zirconia" refers to various stoichiometries for zirconium oxides, most typically $ZrO_2$, and may also be known as zirconium oxide or zirconium dioxide. The zirconia may contain up to 20 weight percent of oxides of other chemical elements such as, for example, oxides of yttrium (e.g., $Y_2O_3$).

The term "ceramic" means an inorganic non-metallic material that is produced by application of heat. Ceramics are usually hard, porous and brittle and, in contrast to glasses or glass ceramics, display an essentially purely crystalline structure.

The term "glass ceramic" means an inorganic non-metallic material where one or more crystalline phases are surrounded by a glassy phase.

The term "dental milling disc/blank" is a solid form of various shapes, e.g., disc or block or any shape that can be fixedly attached to the dental milling machine. Diameter for disc shape is usually 100-90 mm, with various thickness of 10-25 mm for multiple-prostheses milling. Blocks may be about 20 mm to about 30 mm in two dimensions (width and height), for example, and may be of a certain length in a third dimension.

The term "thickness" when used in reference to the green body, green body dental prosthesis, or the dental prosthesis refers to a particular direction aligned in the thickness or height of the green body or dental prosthesis, and can be from a lower layer or portion of the green body or dental prosthesis (corresponding to an cervical area of a tooth) to an upper layer or portion of the green body or dental prosthesis (corresponding to a incisal area of a tooth), such as an increasing translucency or decreasing chroma from the lower layer or portion (cervical) to the upper layer or portion (incisal).

Description

The current invention relates to a method of fabricating yttria stabilized polycrystalline zirconia discs/blanks to produce dental prostheses using CAD/CAM processes. The blanks contain a gradually increasing amount of yttria ($Y_2O_3$) where the incisal area of a tooth will be, resulting in more translucency and less color intensity/chroma, thereby better replicating what is typically found in the human tooth. This inventive ceramic disc/blank does not have any optical gradation properties in the green stage before primary sintering. Dental prostheses made of this material take on similar optical properties found in natural human teeth only after the coloring and sintering stage.

Computer-aided design/computer-aided manufacturing (CAD/CAM) processes and equipment have been widely utilized in the dental industry. In these processes a three-dimensional image of a stump of a tooth is created along with the teeth surrounding the stump in an effort to create a dental restoration (dental prosthesis) which is to be placed over the stump. This image is displayed on a computer screen. Based on the stump and surrounding teeth, the dental technician may then select a tooth from a plurality of tooth library forms stored in the computer to best fit the stump. The selected tooth is projected onto the stump until an optimum positioning and fit of the dental restoration is achieved by dental design software. The digital data concerning the dental restoration thus formed are supplied to a numerically controlled milling machine operating in three dimensions. The milling machine cuts a blank of ceramic material, typically zirconia, into the dental restoration design based on the data supplied.

Referring to FIG. 1, a method for fabricating a dental block is shown in steps 1-5; while a method for forming a dental prosthesis from the dental block is shown in steps 6-11. The starting zirconia material (3YS, 3YS-E, Px242, Tosoh Corp, Japan) consists of fairly uniform particles thoroughly dispersed to be essentially free of agglomerates such that it will sinter predictably and isotropically without appreciable distortion. The particle size D50 may be in the range of about 0.1 to 1.0 micron. The zirconia and yttria can be formed into a desired shape (see 20, 24, 25 and 25b in FIGS. 2a-2e by way of example), and the amount of ytrria can be increased through a thickness of the shape or dental block. As show in table 1, zirconia material for each different layer can be prepared by combining the zirconia and yttria together, while increasing the amount of yttria (Y2O3) in successive layers so that the amount of yttria is increased incrementally from a lower layer to an upper layer. The amount of yttria (Y2O3) in the lower layer can be 4.5-6 wt % in one aspect, or 4.95-5.35 wt % in another aspect. The next upper layer has a higher amount of yttria (Y2O3) within the practical limit. The top layer can have as high as 6.0-7.0 wt % of Y2O3, and it further can have as high as 7.0-8.0 wt % of Y2O3, and yet it further can have as high as 8.0-9.0 wt % of Y2O3, and it can even have as high as 9.0-10 wt % of Y2O3. Incremental addition of yttria (Y2O3) can be done with the co-precipitation of Y2O3 with ZrO2 salts or by coating of the ZrO2 grains with Y2O3.

TABLE 1

| | Zirconia | Yttria (Y2O3) | Color Pigment |
|---|---|---|---|
| C | ZrO2 + HfO2 + Y2O3 > 99.00 wt % | 6.0-7.0 wt % | 0.0 wt % |
| B | ZrO2 + HfO2 + Y2O3 > 99.00 wt % | 5.5-6.0 wt % | 0.0 wt % |
| A | ZrO2 + HfO2 + Y2O3 > 99.00 wt % | 4.9-5.35 wt % | 0.0 wt % |

Referring to FIGS. 2a-2d, zirconia powders and yttria are combined with or without a binder and pressed into blocks or similar shapes to form a green body 20. Each layer or portions 21, 22, 23 of the green body 20 is deposited using any of the known forming methods including, but not limited to, pressing, uniaxial or isostatic, extrusion, slip casting, gel casting, pressure filtration and injection molding. In one aspect, the method to consolidate green body 20 is cold isostatic pressing (CIP) and pressure filtration which is associated with one of the highest degrees of homogeneity attainable in green density. The zirconia and yttria of each layer can be separately combined and formed. Thus, the layers have different chemical compositions, namely with different amounts of yttria. The multiple different layers can be separate and discrete and distinct layers connected together but with a boundary therebetween and characterized by distinct changes in the amount of yttria; or the multiple different layers can form a region or layer with a more continuous change in the amount of yttria through the thickness of the region or layer, with the multiple different layers being indistinct and without any clear boundary therebetween. The height of the layers can be any proportion, and can be in a decreasing manner from the lower layer to the upper layer so that the lower layer is thicker and the upper layer is thinner (A>B>C). For example, bottom layer 21 can be 2-5 mm thick, and the middle layer 22 can be 4 mm thick, and the top layer can be 2 mm thick. The top layer 23 can be as thin as 2 mm, and it further can be as thin as 1 mm, and it further can be as thin as 0.5 mm. The layers can be as many as three layers, and it further can be as many as up to seven to ten layers to create a natural transition of optical changes. The green body 20 is formed into any desired shape and configuration (such as a disc or puck 20, an elongated block or bar 24, or a square or rectangular block 25) which will render a dental restoration. The layers can be parallel and have a constant thickness, as shown in FIGS. 2a-2d. Alternatively, the layers can have a non-uniform thickness as shown in block 25b in FIG. 2e. Fairly uniform, free flowing particles should be used for pressing or molding. Binders such as polyvinyl alcohol (PVA), polyethylene glycol, wax, TEOS, and the like may be mixed with zirconia powders to retain the shape of the green bodies during and after forming. The invention is in no way limited to the stated binders, and any suitable binder may be used herein to achieve the desired results. The density of the green body 20 is from about fifty percent (50%) to about seventy-five percent (75%) percent of theoretical density. In accordance with the process herein, after forming the zirconia ceramic powder into green body 20, the body 20 may be machined to the shape of a dental restoration or green dental prosthesis 26 such as a coping or full contour prosthesis, using a computer assisted miller.

For purposes of example, a full contour zirconia tooth 26 will be used to explain the process herein. The shape of the full contour zirconia tooth 26 is determined from data received by scanning the tooth or die of the tooth to be restored. The size of the tooth which is machined is oversized to allow for shrinkage when the full contour zirconia tooth 26 is sintered. The linear dimensions of the zirconia prosthesis 26 is typically about twenty percent (20%) to about twenty-five percent (25%) larger than the size of the final tooth since the linear shrinkage of the tooth after sintering is about sixteen percent (16.67%, =((1.20−1)/1.20) to about twenty percent (20%, =((1.25−1)/1.25). The full contour zirconia green body tooth 26 is then sintered to full density at a temperature around 1300-1500° C. depending on the grain size of the zirconia.

The green body 20 is soft-sintered to a bisque density that is between about fifty percent (50%) and about seventy-five percent (75%) of the final density. The disc/blank 20 is treated with heat for millable strength with temperature ranging from about 900 to about 1100° C. for a holding period of about 1 to 3 hours. A pre-sintered dental ceramic article or green dental prosthesis 26 typically has a density (usually 3.0 g/cm3 for an Yttrium stabilized ZrO2 ceramic) that is less compared to a completely sintered dental ceramic article or dental prosthesis 32 (usually 6.1 g/cm3 for an Yttrium stabilized ZrO2 ceramic). After this pre-sintering stage, the current invention takes on a generally opaque appearance over the entire surface. The green body 20 and/or 26, or layers thereof, can be substantially opaque with a substantially consistent optical characteristic of non-translucency with respect to visible light across the layers. (Various different dental prostheses are shown in FIGS. 4a-4d with different numbers of layers and different thicknesses of layers; and even different orientation of layers; with the layers having different optical properties of translucency and/or chroma between adjacent layers.)

Figure 3A:
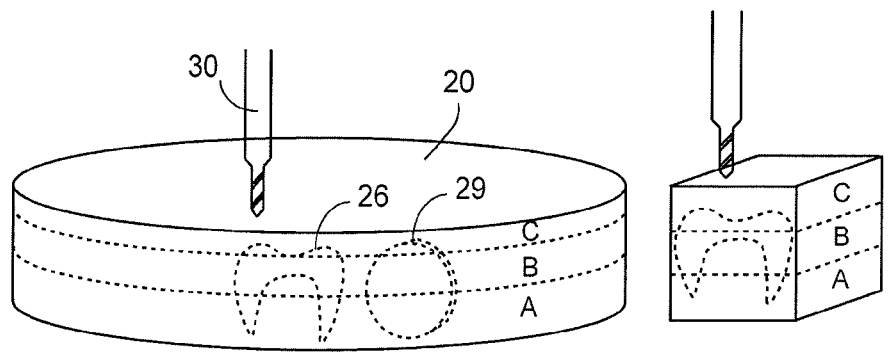
FIG. 3a is a schematic perspective view of the green body dental block of FIG. 1 shown with multiple different layers and a dental prosthesis and a sample disc to be milled therefrom.
Figures 3B, 3C:
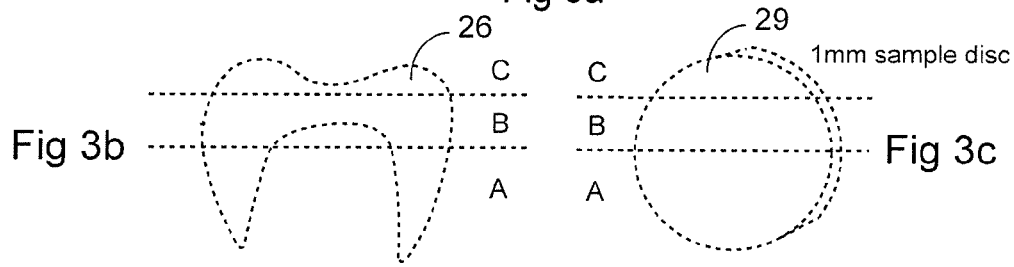
FIG. 3b is a schematic view of a green body dental prosthesis milled from the green body dental blank of FIG. 3a shown with multiple different layers.
FIG. 3c is a schematic view of a green body sample disc milled from the green body dental blank of FIG. 3a shown with multiple different layers.
Figure 3D:
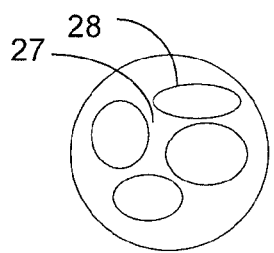
FIG. 3d is a schematic view of a portion of the green body showing the open pores between grains thereof.

In the pre-sintering stage, the inventors found that the amount of open pores 27 between grains 28 (FIG. 3d) are important because it determines the efficiency level of coloring at the later stage. The more open pores 27, the weaker the green body 26, but higher coloring efficiency, and the less the amount of open pores 27, the stronger the green body but lower coloring efficiency. The level of open pores 27 that contain air can determine the desired green body strength for millability and the efficiency of green body 26 coloring. The level of amount of open pores 27 can be expressed, for example, by L* value from the CIE L*a*b* colorimetric system.

Figure 8:
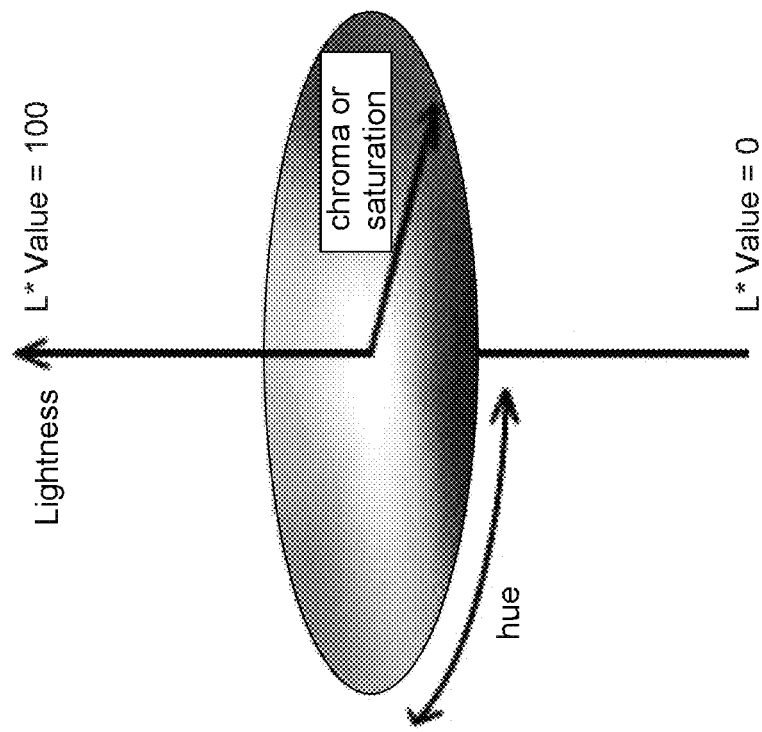
FIG. 8 is a schematic of the CIE L*a*b* colorimetric system to help understand the color aspect of the current invention.
Figure 8:
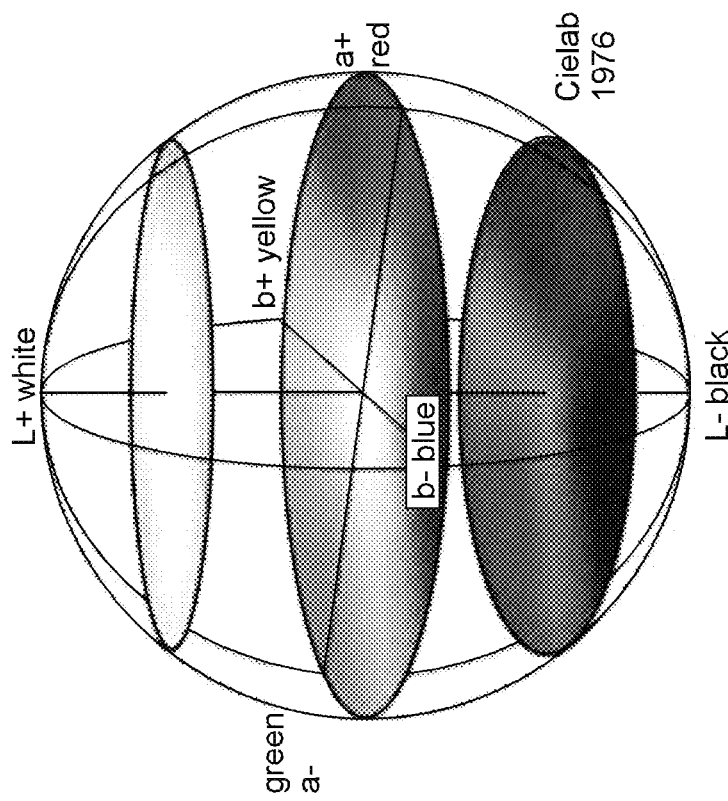

The L*a*b* colorimetric system in FIG. 8 was standardized in 1976 by Commission Internationale de l'Eclairage (CIE). In the system, a lightness/brightness is defined as L* and expressed by a numerical value of from 0 to 100, in which L*=0 means that the color is complete black, and L*=100 means that the color is complete white.

When advanced ceramics with poly-crystal structures contain substantially no residual pores after being fully sintered, the L* value goes up to as high as 60-85 for the samples with thickness of 1 mm, thereby characterized with good light transmission. When the zirconia green body 20 is partly sintered, i.e. in a pre-sintered stage, it contains open pores/air which causes the diffusion of light, resulting in a much lower L* value number.

The inventors discovered that the higher this L* value number for the zirconia green body 20, the harder it is to mill and more difficult it is to be penetrated with color-ion liquids. The lower the number, the weaker the green body 20, causing cracks and chipping during the milling process and making it more difficult to control the coloring consistency at later stage. It was found that the ideal L* value, when expressed in CIE L*a*b* colorimetric system in a standard illuminant D65, is between 10 and 20 in one aspect, and 15 and 20 in another aspect.

Figure 9A:
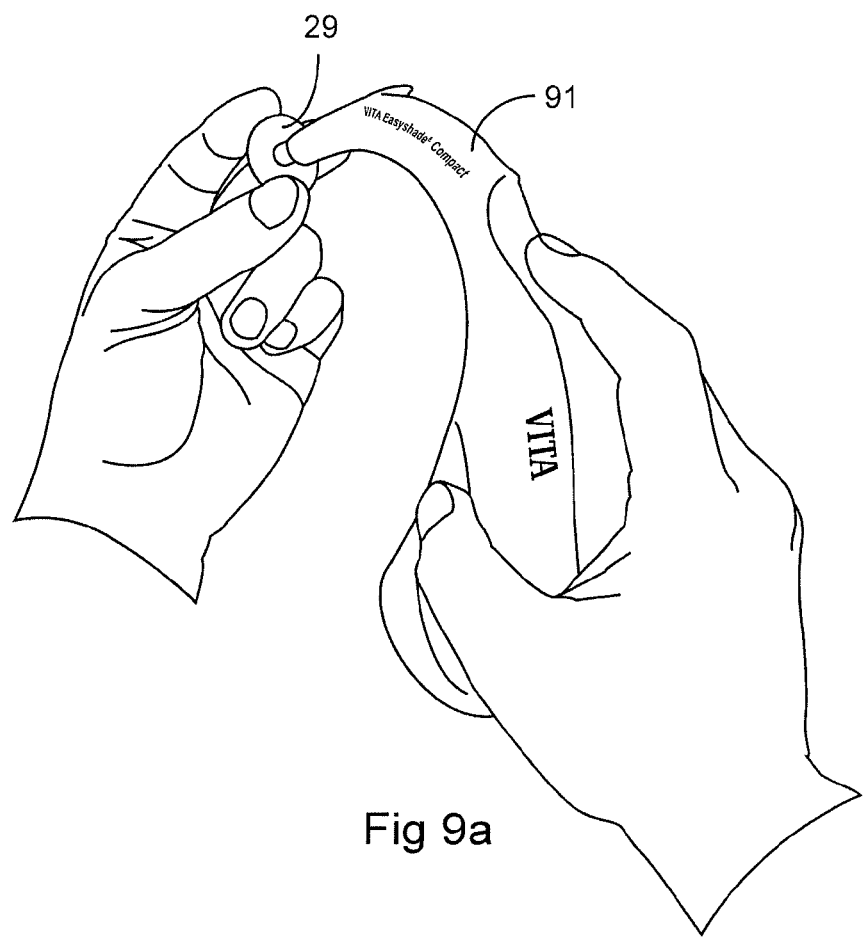
FIGS. 9*a* and 9*b* are schematic views of a color chroma measuring method using a hand-held spectrophotometer.
Figure 9B:
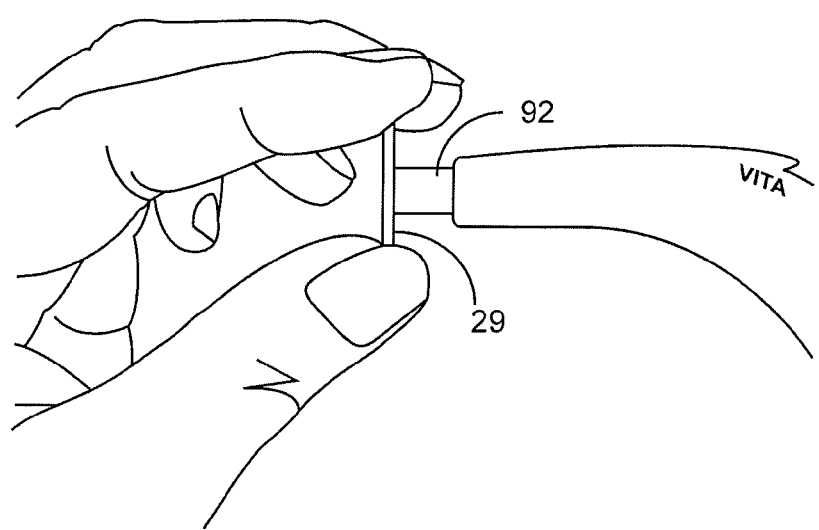
Figure 10A:
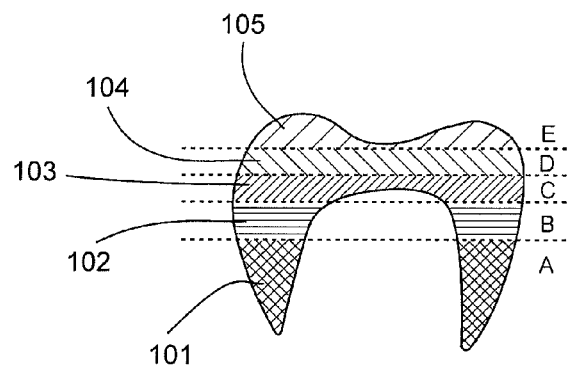
FIG. 10*a* is a schematic cross-sectional side view of a dental prosthesis having different color chroma layers.
Figure 10B:
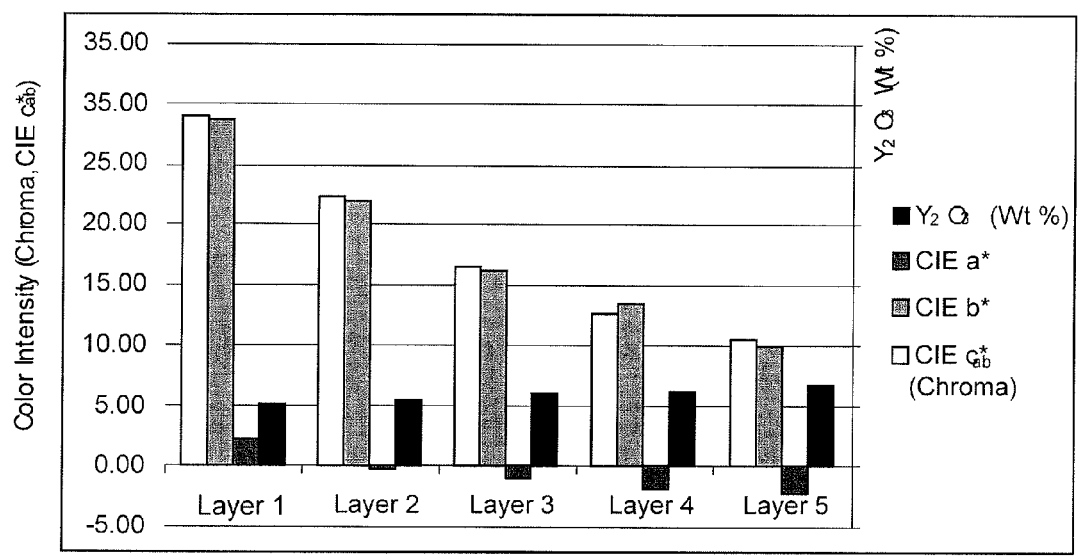
FIG. 10*b* is a graphical representation showing the color chroma level for samples A, B, C, D, and E of FIG. 10*a*.

Specifically, when measured for L* value of a CIE L*a*b* colorimetric system using the VITA Easyshade® Compact spectrophotometer (VITA, Germany, www.vita-zahnfabrik.com) 91 as in FIG. 9, which is most widely used for color analysis in dental office/laboratory, the L* value of the current invention, from a sample 29 with a diameter of 15 mm and thickness of 1.00 to 1.30 mm, is 10-20 in one aspect or 15-20 in another aspect from single and/or multi mode. The samples were measured according to the user manual in such a way as for the reading tip 92 of the spectrophotometer 91 to be set flush with, in close touching contact, and perpendicular to the measured surface of the pre-sintered zirconia sample 29. Since the VITA Easyshade has a built-in light source inside the tip area, the ideal L* value of 10-20 or 15-20 were independent of the amount of light in a normal office room setting.

The pre-sintered/soft-sintered disc/block 20, 24, 25 is then machined with a computer assisted miller 30 to a desired tooth shape 26, which is oversized to account for anticipated shrinkage during the sintering stage, and sintered to a final density rendering a high strength dental restorative material or dental prosthesis 32. The soft-sintered state of the disc/blanks 20 allows for easy milling into complex or elaborate shapes 26.

Depending upon the density of the production batches, the linear dimensions of the green body prosthesis 26 may range from a size that is about twenty percent (20%) to about twenty five percent (25%) larger than the size of the final prosthesis 32 based on the linear shrinkage of the bisque body 26 which may range from about sixteen percent (16.67%, =((1.20−1)/1.20) to about twenty percent (20%, =((1.25−1)/1.25) shrinkage thereof. The green body prosthesis 26 is then sintered to full density at the temperature-time cycle specific for the zirconia grain size used, e.g., for 0.1-1.0 micron, at about 1300-1600° C. for about 1 to 3 hours.

Figure 3E:
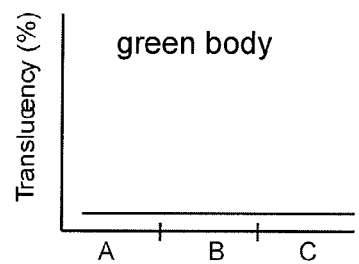
FIG. 3e is a graph of the translucency of the multiple different layers of the green body dental prosthesis of FIG. 3b.
Figure 3F:
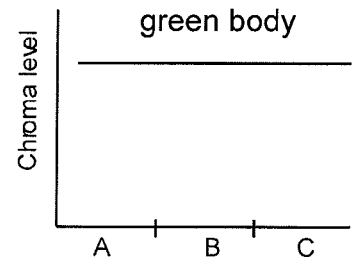
FIG. 3f is a graph of the chroma level of the multiple different layers of the green body dental prosthesis of FIG. 3b.
Figure 3K:
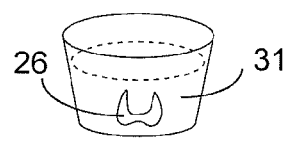
FIG. 3*k* is a schematic view showing the green body dental prosthesis of FIG. 3*b* being colored.
Figures 3G, 3H:
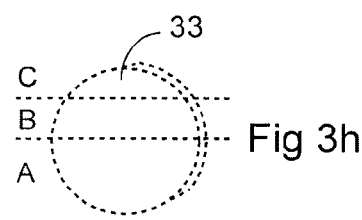
FIG. 3g is schematic view of a dental prosthesis milled from the green body dental blank of FIG. 3a shown with multiple different layers.
FIG. 3h is a schematic view of a sample disc milled from the green body dental blank of FIG. 3a shown with multiple different layers.
Figure 3I:
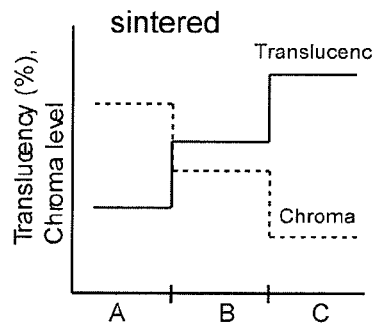
FIG. 3*i* is a graph showing translucency and chroma levels for the dental prosthesis of FIG. 3*g*.
Figure 3J:
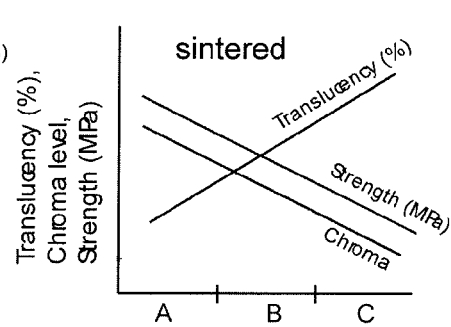
FIG. 3*j* is a graph showing translucency, chromal level and strength across the multiple different layers of the dental prosthesis of FIG. 3*g*.
Figure 4A:
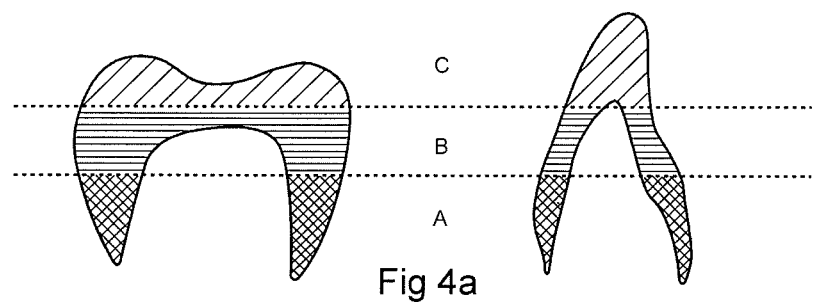
FIGS. 4*a*-*d* are cross-sectional side schematic view of dental prostheses of the present invention with the layers thereof having different optical properties.
Figure 4B:
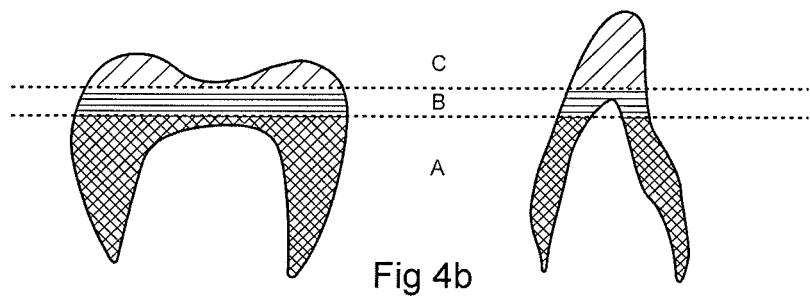
Figure 4C:
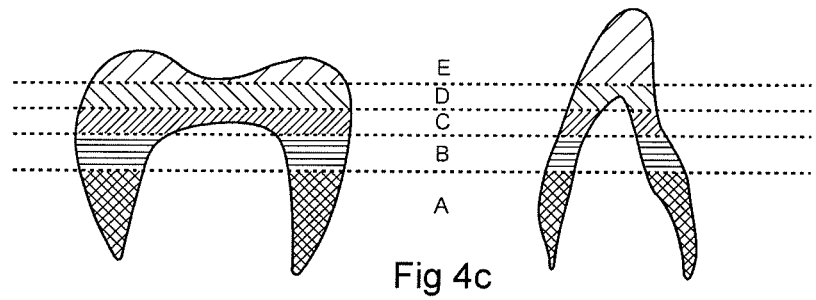
Figure 4D:
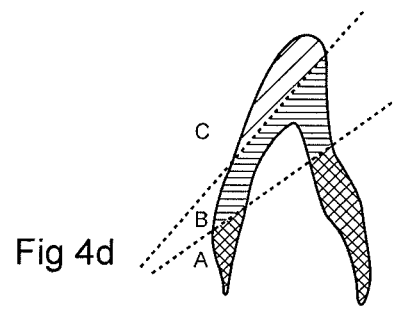
Figure 5A:
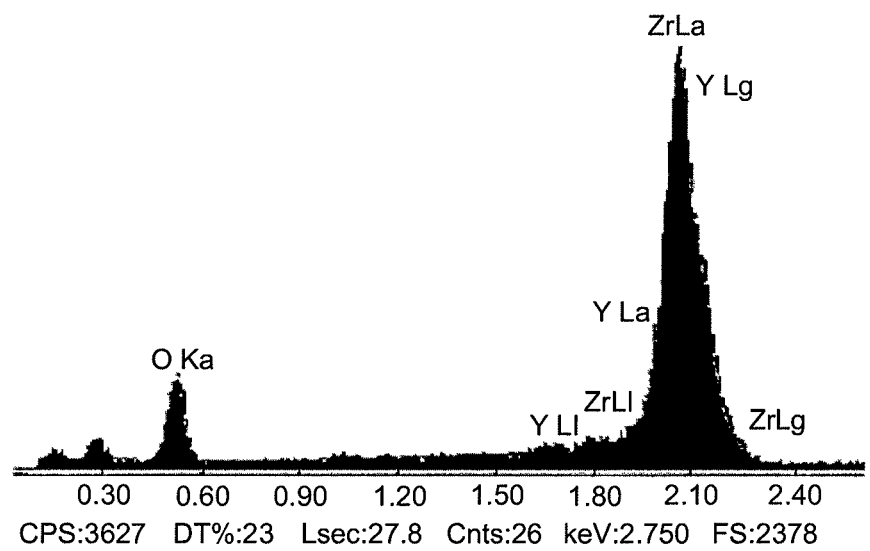
FIGS. 5*a* and *b* are graphs of representative x-ray diffraction pattern for an exemplary zirconia disc of the present invention.
Figure 5B:
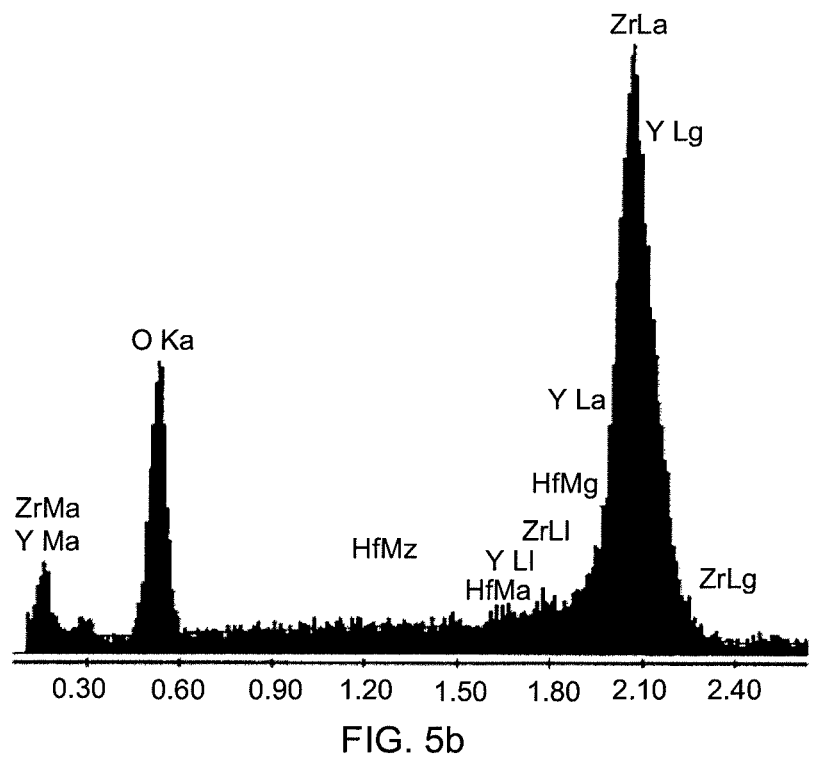

Unlike the glass and glass-ceramic materials, coloring of the current invention is done after pre-sintering, that is, in a porous and partially sintered state. For all the glass ceramic materials, color pigments are added to the glass matrix and then glass ceramic undergoes heat treatments. The coloring of the current invention involves the use of aqueous color solution. This coloring of zirconia 26 is processed in the porous or absorbent state, which is characterized in that metal ion solutions or metal complex solutions are used for the coloring. Aqueous or alcoholic metal solutions of Fe, Mn, Cr can be used, for example as chlorides or acetates. Milled green prostheses 26 are dipped into the solution or can be brushed for specific tooth shade effects. This zirconia green body 20 and milled chalky parts 26 are not a ceramic compound with predetermined optical properties, instead they are a ceramic compound without predetermined optical properties. They are chalky, opaque, do not have translucency as shown in FIG. 3e, and do not have difference in brightness, reflectance or color between the upper and lower portions of the disc/blank as shown in FIG. 3f.

Pre-sintered and milled zirconia prosthesis 26 shrinks during a (primary) sintering step, that is, if an adequate temperature is applied. The sintering temperature to be applied depends on the ceramic material chosen. For $ZrO_2$ based ceramics a typical sintering temperature range is about 1300° C. to about 1600° C. $Al_2O_3$ based ceramics are typically sintered in a temperature range of about 1300° C. to about 1700° C. Glass ceramic materials are typically sintered in a range of about 700 to about 1100° C. for about 1 to about 3 h. This primary sintering includes the densification of a porous material to a less porous material (or a material having less cells) having a higher density, and in some cases sintering may also include changes of the material phase composition (for example, a partial conversion of an amorphous phase toward a crystalline phase).

Pre-sintered, yttrium-stabilized zirconia ceramics 20 are available for use with CAD/CAM technologies. Zirconia ceramic can be used for frameworks of crowns and FDP (fixed dental prosthesis) in the posterior region. Unfortunately, current processing technologies cannot make zirconia frameworks or full contour crowns as translucent as natural teeth.

Translucency is the relative amount of light transmitted through the material. In a natural tooth, translucency is identified when a noticeable amount of light passes through its proximal and/or incisal aspect due to the presence of only enamel or a high proportion of enamel compared to the underlying dentin. In the cervical aspect of the teeth, where the dentin is thicker, the light transmission will be reduced. The translucency of the enamel and dentin is wavelength dependent; the higher the wavelength, the higher the translucency value.

The human tooth structure scatters much of the incidental light. In such light scattering media, the intensity of the incidence light flux is diminished as the light passes through the medium. The enamel and dentin are not totally homogeneous at the histological level, which affects scattering and absorption of the light.

Figure 7A:
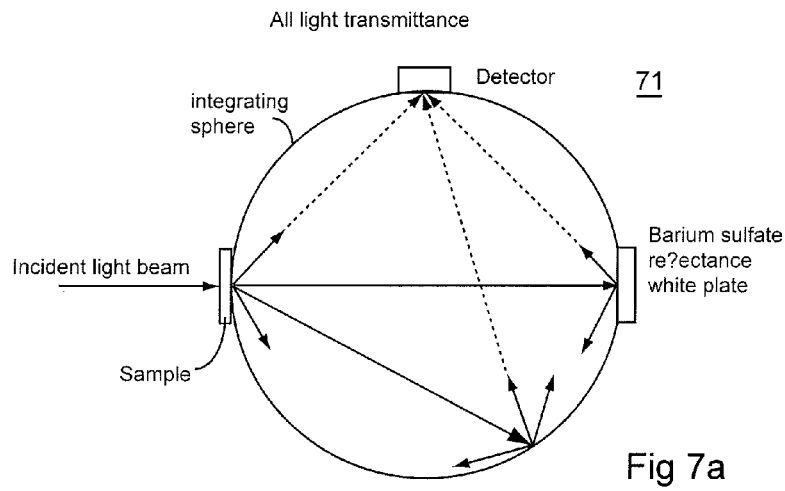
FIG. 7*a* is a schematic diagram for measuring translucency of samples using a high-end spectrophotometer with an integrating sphere.

One method of measuring translucency is by determining total transmission, including scattering, using a spectrophotometer with an integrating sphere as shown in FIG. 7a. Translucency of a material can be expressed as a transmission coefficient or total (direct and diffused) light transmittance (%) as the relative amount of light passing through the unit thickness of the material. To measure the different level of translucency of each layer of the current invention, total light transmittance was measured by a double beam-system spectrophotometer 71 as in FIG. 7a (LAMBDA 35, UV/Vis Spectrophotometers manufactured by Perkin Elmer, USA) based on the "Standard test method for transmittance and color by spectrophotometer using hemispherical geometry" of ASTM E1348-11 and "Materials and articles in contact with foodstuffs—Test methods for translucency of ceramic articles" of Dansk Standard/EN 1184.

Figure 6A:
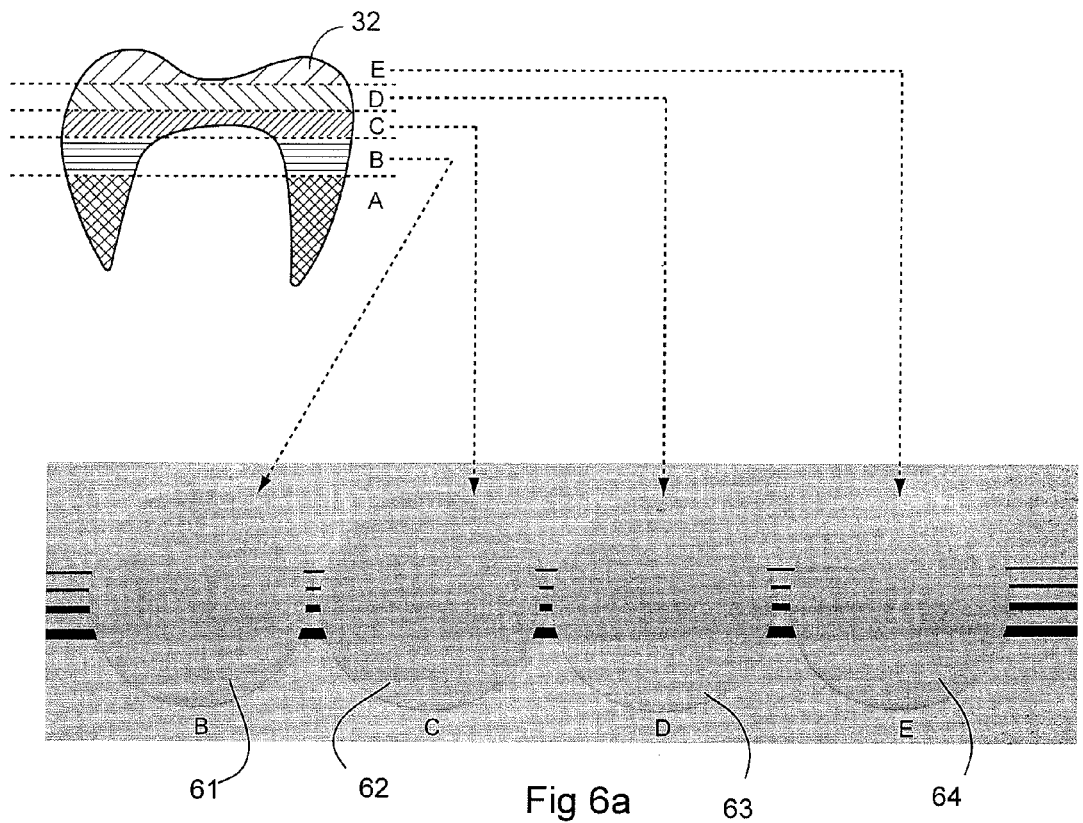
FIG. 6*a* is a schematic showing a qualitative translucency assessment of the current invention after final sintering.
Figure 6B:
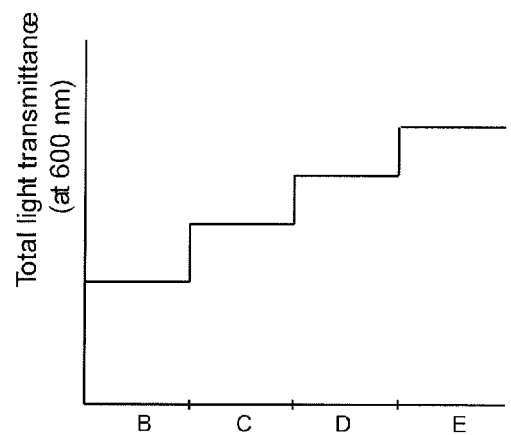
FIG. 6*b* is a graph depicting the translucency of the current invention at 600 nm for each level of differing material in the restoration after the final sintering stage; p

Measurement samples 61-64 used in FIG. 6a were samples obtained by processing a fully sintered (holding time 2 hours at 1,530° C. with regular sintering in the air, no post HIP processing) body of the current zirconia invention to a thickness of 0.6 mm (with a diameter of 20 mm) and mirror polishing both sides with 2500-grit silicon carbide paper (Wetordry Tri-M-ite Paper, 2500A, 3M Company, St. Paul, Minn.). All the samples were cleaned with isopropyl alcohol before light transmittance measurement. Light emitted from a light source (deuterium lamp and halogen lamp) was passed through a sample and scattered, and all light transmission amount was measured using an integrating sphere. Samples of small plates a, b, c and d from each layer of the current invention 20 as shown in FIG. 6a have incrementally increasing amounts of yttria (Y2O3) as a component. Each material constituting each layer B, C, D and E was used to make small plates b 61, c 62, d 63 and e 64 of 0.6 mm in thickness. As yttria (Y2O3) contents increase, so does total light transmittance as shown in FIG. 6b.

Visible light which had passed through the sample was collected with an integrating sphere to determine the intensity of the visible light (I). On the other hand, the intensity of visible light ($I_0$) was measured without placing the sample. The total light transmittance was calculated in terms of the proportion of the former to the latter intensity (=I/$I_0$). A transmission spectrum and digital data record were obtained for each measurement with the light beam entering the samples. Four measurements were made with each sample rotated 90° from the previous measurement.

Figure 7B:
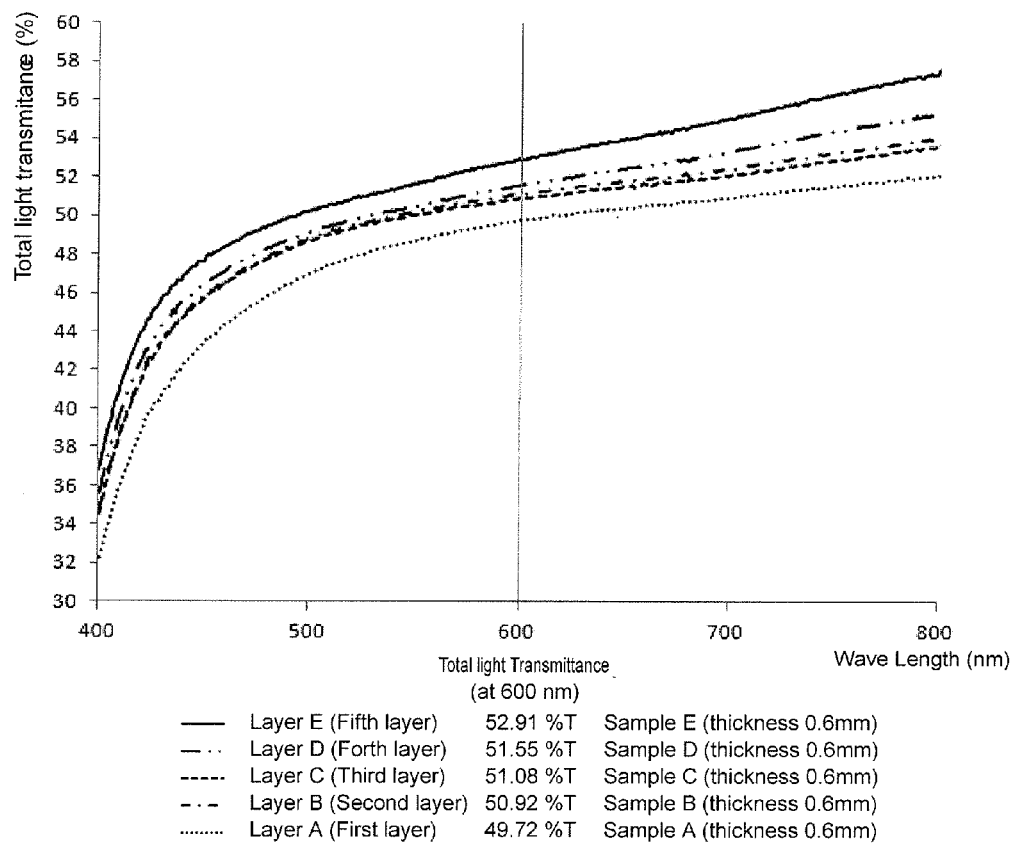
FIG. 7*b* is a graphical representation of light transmittance (%) versus wavelength (nm) at 400 to 800 nm for each level of differing material in the restoration after final sintering; levels are labeled as samples A, B, C, D, and E of the current invention.

A measurement wavelength region was from 400 to 800 nm, and total light transmittance in the present invention was a transmittance at a wavelength of 600 nm in a visible light region as shown in table 2 and FIG. 7b. The decrease in total light transmittance with decreasing wavelength is due to the increase in light scattering as indicated by the Rayleigh scattering equation. Similar results were reported for dental porcelains.

Test result of all light transmittance is presented in the following comparative example.

Comparative Example

TABLE 2

| Samples of 0.6 mm thick | Stabilizer (Y2O3) contents Wt % | sintering temperature ° C. | Density of sintered body g/cm3 | Flexural strength* Mpa | total light transmittance % |
|---|---|---|---|---|---|
| Sample E (5th layer) | 7.0 | 1530 | 99.8 | 925 | 52.91 |
| Sample D (4th layer) | 6.5 | 1530 | 99.8 | 1021 | 51.55 |
| Sample C (3rd layer) | 6.0 | 1530 | 99.8 | 1152 | 51.08 |
| Sample B (2nd layer) | 5.5 | 1530 | 99.8 | 1253 | 50.92 |
| Sample A (1st layer) | 4.9-5.35 | 1530 | 99.8 | 1385 | 49.72 |

The inventors discovered that the level of total light transmittance (%) increased when yttria contents were increased towards the next upper layers. As can be seen from the table 2, each upper layer has a higher light transmittance than all layers below it. All of the 0.6 mm thick samples have a higher transmittance level that is approximately 12-16% higher than 1.0 mm thick samples tested with the same procedures and methods.

The bottom layer (first layer) 21 of the current invention disc/blank in which cervical aspect of dental crown & bridge would be located has the lowest translucency level after primary sintering, representing the thinnest enamel and thickest dentin portion of a human tooth. After primary sintering, translucency levels gradually increase towards the top portion 23 of the current invention dental disc/blank. The top portion 23 has the highest level of translucency after primary sintering in which the incisal aspect of dental prosthesis would be located.

The current invention is technically distinctive and differentiated from other multi-layered ceramics in the way the graded translucency level is created. One type of multi-layered ceramic currently available in the market comprises small sized rectangular blocks with pre-determined colors, for example, A1, A2, etc, that all have chemically homogenous components for each layer in which, less colorants/color pigments are used towards the incisal area to produce a seemingly more translucent effect. The yttria (Y2O3) of the present invention is not a colorant, it does not produce any color effect. The other material type is known that has a different translucency level from the bottom (cervical) to the top (incisal).

Whereas, the green body dental block of the current invention does not have any noticeable optical characteristics, except that it is generally an opaque disk/blank without pre-determined color. Even if there are more yttria (Y2O3) contents towards the incisal area of the current invention, the translucency level before primary sintering is still the same for each layer, being only very opaque and substantially almost no translucency throughout the whole green body 20, 26 as shown in FIG. 3e. The increased translucency effect can take place only after the primary sintering stage is complete as in dental prosthesis 32.

Prior art teaches that the reason why each layer should not have a different chemical composition, but should only have a variation of contents of specific color pigments, is because of the coefficiency of thermal expansion. The dental industry is characterized by accurate fit of the restorations with no distortion of the sintered prosthesis. All of the dental ceramic materials have their unique pattern of response to heat when treated with high temperature for strengthening. The way each material behaves are all different, including but not limited to, the speed by which porous ceramic material shrinks and the absolute temperature level that requires full densification, etc. If the chemical composition of each layer is different thereby creating a different CTE (Coefficiency of Thermal Expansion), sintering temperature, or sintering speed, then the final restoration would not fit in the patient's mouth. This is why all prior art of layered ceramics use the same chemical composition throughout the blank, and put only different amounts of tooth color pigments from the bottom portion to the top portion.

The current invention was able to overcome this area of CTE related problems inspite of having different chemical compositions with different levels of yttria (Y2O3) contents by individually characterizing, for example, coating powder particles of each layer.

Yttria (Y2O3) is just an example of some of the additives/components that increase the translucency of the incisal/top area of dental blanks. Other examples that produces the similar effect are spinel ($MgAl_2O_4$), $Al_2O_3$, $SiO_2$, $TiO_2$, $B_2O_3$, $Na_2O_3$, $Y_2O_3$, $K_2O$, $CeO_2$, $MgAl_2O_4$, $MgO$, $HfO_2$, etc.

Natural teeth are typically composed of a variety of colors, and a gradation occurs in an individual tooth from the gingival margin to the incisal edge depending upon the ratio between enamel and dentin thickness.

One of the most exacting and time consuming aspects of dental restorations, whether involving direct or indirect placement techniques, is that of properly matching the color of the restoration to that of the original tooth. In the context of clinical dentistry, the term "color" involves three discrete concepts: hue, chroma and value. Hue is the dimension of color that enables us to distinguish one family of color from another; chroma defines the relative intensity/saturation of a particular color, i.e., the more intense a color is, the higher its chroma level; and value describes the relative whiteness or blackness of a particular color, i.e., the brighter the color, the higher its value.

Color is often defined in terms of its CIELAB lightness value, $L^*$, its CIELAB chroma value, $C^*$ and its CIELAB hue value, h. "CIE" stands for the Commission Internationale de l'Eclairage and its CIELAB $L^*$, $C^*$ and h values are well known and widely used. "Lightness", $L^*$ value, is a measure of the amount of light/brightness reflected from a surface, that is, the amount of white or black in a color, its lightness or darkness. "Chroma", $C^*$, is a measure of the intensity of a color, i.e. the extent to which it is either a pastel color or a strong color or something in between. "Hue", h, is a measure of how reddish, yellowish, greenish or bluish a color is.

Color matching in dentistry is routinely performed with a visual method. However, instrumental color measurement can render useful information that can aid visual color matching. The Commission Internationale de l'Eclairage (CIE) refined color space in 1976 as shown in FIG. 8. CIE $L^*$ value is a measure of the lightness of an object such that a perfect black has a CIE $L^*$ value of zero and a perfect reflecting diffuser (white) has a CIE $L^*$ value of 100. CIE $a^*$ value is a measure of redness (positive value) or greenness (negative value), and CIE $b^*$ value is a measure of yellowness (positive value) or blueness (negative value). As shown in FIG. 8, The black vertical line is the $L^*$ value intensity axis, the hue is given by an angle from the $L^*$ value intensity axis and the chroma/saturation is the distance from the $L^*$ value intensity axis to the color point (i.e., the radius). The larger the numerical value of each of $a^*$ and $b^*$ is, the brighter the color becomes, whereas when the smaller the numerical value of each of $a^*$ and $b^*$, the duller the color becomes.

Spectrophotometric color measurements differ depending on the measuring geometry and the illuminant. Therefore, when any color measurements are made with an instrument, measured color values are sensitive to the methods employed. Several standard illuminants have been used to measure the color of dental materials. Standard illuminant D65 represents a phase of daylight with a correlated color temperature of approximately 6500 K, illuminant A represents light from the full radiator at absolute temperature 2856 K, and illuminant F2 represents light from fluorescent lamp of medium color temperature of 4230 K. Two standard illuminants are recommended for use in colorimetry. Illuminant A should be used in all applications of colorimetry involving the incandescent lighting, and D65 should be used in all colorimetric calculations requiring representative day light.

To standardize the light source mentioned above and easily calculate the chroma level VITA Easyshade® Compact spectrophotometer (VITA, Germany, www.vita-zahnfabrik.com) was used as in FIG. 9.

Chroma level was calculated as $C^*ab=(a^{*2}+b^{*2})^{1/2}$ according to "Colorimetry—technical report. CIE Pub. No. 15, 3rd ed. Vienna: Bureau Central de la CIE; 2004"

The inventors found out that an increased amount of Y2O3 within a practical limit (0.1-3.0 wt %) for each layer as an additive in the zirconia (ZrO2) body produces a sintered body that has lower intensity in chroma after being dipped into the color-ion solution for shading effect. The more Y2O3 is used within the practical limit, the sintered body becomes lighter in color intensity/chroma.

For example, as seen in the following table 3, the first layer 101 in which the cervical aspect of a tooth will be located has the strongest color intensity/chroma and the fifth layer 105 in which the incisal portion of a tooth would be located has the weakest color intensity/chroma. When dipped into a specific color liquid 31, sample a (first layer 101) produced a slightly dark redish brown color after primary sintering, whereas the sample c (third layer 103) produced a moderately redish brown color, and e (fifth layer 105) produced a sintered body with a light ivory brown color. When each of the different layers of zirconia body 21, 22, 23, with an increasing amount of Y2O3, was deposited into one body 20, 26, 29 and dipped into a specific color (hue) liquid 31, the subsequently sintered body 32, 33 showed a graded color intensity (chroma). This means that a layered zirconia body 20, 26, 29 after being dipped into a color liquid 31 would be able to produce a subsequent sintered body 32, 33 that is gradually diminishing in color intensity/chroma from the cervical to incisal direction as is typically found in the human tooth. Color liquids 31 can be pre-made in as many colors as needed, and the milled porous prosthesis 26 can be simply dipped into this liquid 31. In this way the current invention 20 makes it unnecessary to keep all the inventories of blocks/discs 20 of different shades. Thus, the green body dental prosthesis can be dipped into a single color liquid.

TABLE 3

| Samples (thickness 1 mm) | Y2O3 (Wt %) | CIE a* | CIE b* | CIE c*ab |
| --- | --- | --- | --- | --- |
| Sample E (fifth layer E) | 6.50 | −2.4 | 10.2 | 10.4 |
| Sample D (forth layer D) | 6.25 | −1.9 | 13.5 | 12.5 |
| Sample C (third layer C) | 6.00 | −1.2 | 16.4 | 16.4 |
| Sample B (second layer B) | 5.50 | −0.2 | 22.2 | 22.2 |
| Sample A (first layer A) | 5.00 | 2.0 | 28.8 | 28.9 |

The chroma was measured utilizing a VITA spectrophotometer 91 Easy Shade according to the user manual. The tip 92 of the device 91 was flush and perpendicular with sample 29 as shown in FIG. 9. The result was independent of lighting condition in the office room, that is, the measurement reading did not change when measured with or without the indoor (fluorescent) light on.

This feature of a gradual decrease in color intensity/chroma with higher translucency towards the incisal area gives this invention a unique benefit and advantage of being very similar in optical properties to a natural human tooth and is therefore distinly set apart over other monolithic zirconia bodies currently available in the market. Coloring of dental zirconia bodies, until now, has been possible with only two methods. One is using a non-colored zirconia body that is (subsequent to milling but before final sintering) treated with color-ion liquid. The benefit of this method is to be able to avoid the need of keeping a large inventory of different colored blocks/discs. The disadvantage is that the color of the sintered zirconia body is only mono-chromatic since the color-ion responds the same all the way throughout the homogeneous component of the discs/blocks and finally to the dental prosthesis, making a restoration with only one color. The other method is to use a pre-colored blocks in which each layer has already been pre-colored with different levels of color pigments, but the primary components are basically the same. The advantage is to avoid the coloring process, but the disadvantage is the inefficiency associated with large inventories and restrictions on milling many different colored prostheses in one milling sequence. The current invention has the benefits of both methods by the fact that 1) it uses the simple-dipping coloring method which eliminates the inefficiencies associated with inventory issues and 2) sintered results give the graded color intensity/chroma like the pre-colored blocks with different levels of color pigments. This unique feature comes from a disc/blank in which each layer has been prepared hetero-geneously and deposited with different levels of ytrria (Y2O3) contents.

The current invention of layered zirconia body 20 also shows a functionally graded flexural strength. As shown in table 2, the first layer a 101 with the lowest amount (wt %) of yttria (Y2O3) contents shows the highest strength of 1385 MPa, and the fifth layer e 105 with the highest amount of (wt %) of yttria (Y2O3) contents shows the lowest strength of around 925 Mpa. The flexural strength was based on "Implants for surgery-ceramic materials based on yttria-stabilized tetragonal zirconia" of ISO 13356, and the flexural strength was measured by a three-point flexural test.

Figure 11A:
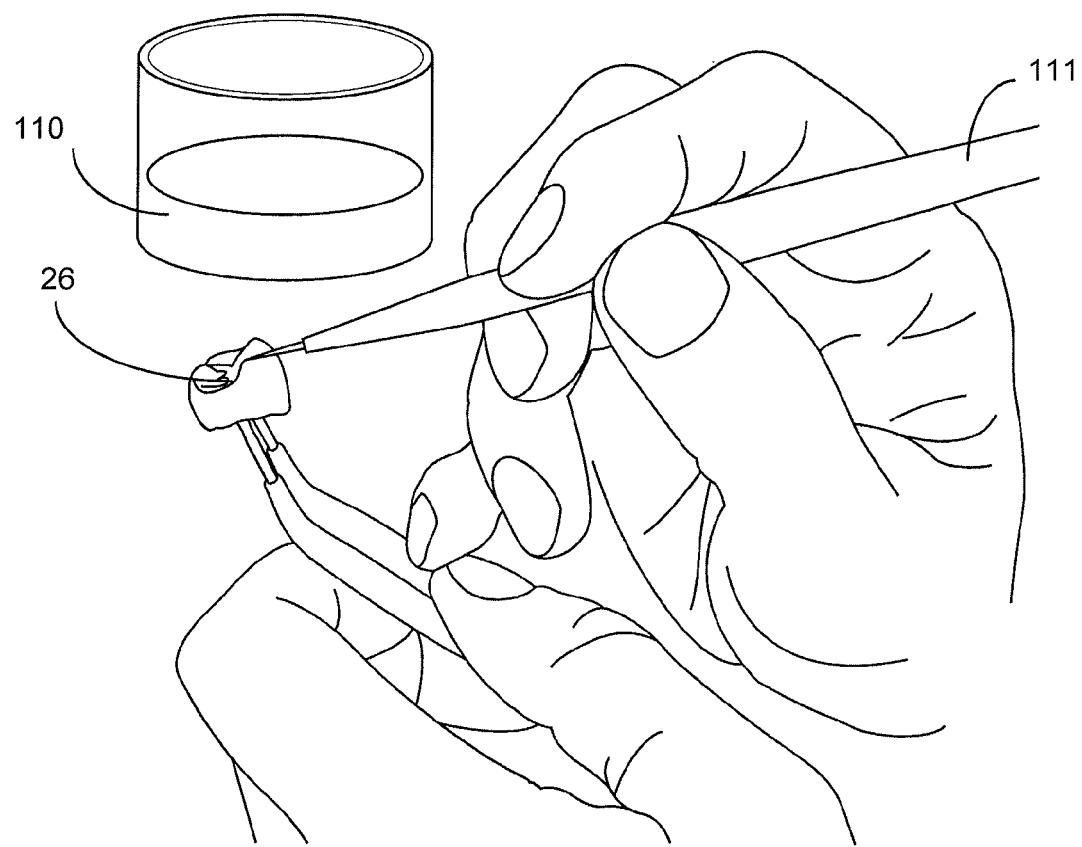
FIGS. 11*a* and *b* are schematic views of coloring of a green body dental prosthesis.
Figure 11B:
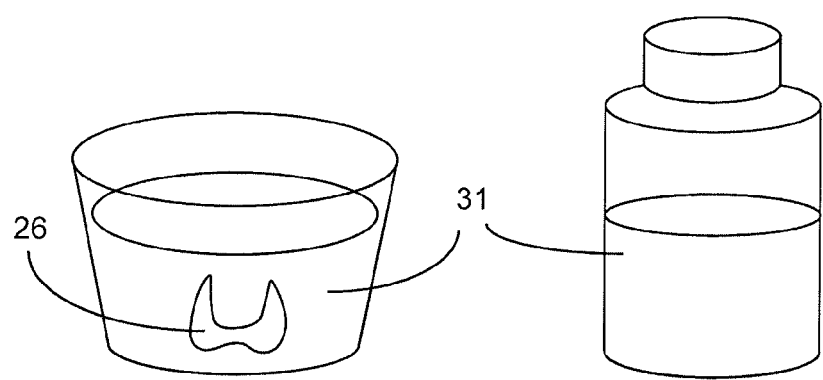

It is already know in the industry that color reproduction of dental prosthesis can be done using the method from U.S. Pat. No. 6,709,694. As shown in FIGS. 11a, and 11b, milled porous dental prosthesis 26, before primary sintering, can be completely immersed in a color-ion liquid 31 for a specific tooth color and then, after a drying time of about 30 minutes, be sintered at temperature of around 1,500° C. in the sintering furnace to produce a color effect of the tooth. The problem with the above mentioned method is that the immersed dental prosthesis body 26 absorbs the coloring liquid 31 in a homogeneous way throughout the entire prosthesis 26, resulting in a sintered prosthesis that has all the same color from the bottom/cervical to the top/incisal direction. It's either in all incisal-light color or all body-intense color. On this starting prosthesis 26, which has only a mono-tone color throughout the sintered body, the dental technician has to add extra colors to create a darker effect for the body and cervical aspect of a tooth. The teaching of this method is a two-step coloring by which an overall light color has to be first created corresponding to the incisal color of a tooth and then a darker body color is created at a separate, subsequent heat treatment process.

What the inventors discovered is a simplified one-step sintering method, while still allowing the creation of a double coloring effect as indicated in the following method; first the liquid 110 is applied on the incisal area only with a brushing method, followed by a smearing time of about 30 seconds, and second the liquid 31 is applied by the immersing method. The components of the first liquid 110 that is brushed on the incisal area are water (40-45 wt %), polyethylene glycol (40-45 wt %) and manganese chloride for av incisal graying effect. Coloring-ions other than colorants for graying effect preferably are not added. The inventors found that polyethylene glycol in the first liquid 110 plays a role of either partly blocking or interfering with the infiltration of the second color liquid 31 into the area applied by the first liquid 110, which is a very useful discovery that has not been taught anywhere. The principle of coloring with color liquids 110 and 31 is that the color ion in the liquid 110 smears through the porous space (about 50-100 nano) of the pre-sintered green zirconia body 26 described in the earlier part of the detailed description of this invention. But when this porous space is already filled with liquid agents like polyethylene glycol, the infiltration process becomes locally deterred and incomplete. As a result, the incisal area covered by the first liquid 110 becomes light in color intensity/chroma presenting more natural tooth color characteristics.

This method can be used for both monolithic zirconia that is all one material/component or multi-layered zirconia bodies with different amounts of yttria (Y2O3) contents. When used with multi-layered zirconia bodies, the result is more aesthetic, since the incisal aspect of the multi-layered zirconia, with increasing amounts of yttria (Y2O3), gives incrementally increased translucency as well.

There should be a certain period of absorbing and drying time of the first liquid 110 of about 0.5 to 2 minutes for optimum results before the application of the second liquid 31. The first liquid can be locally and incisally applied by using a fine tipped brush 111, and the application of the second liquid 31 is usually completed by immersing the green body 26 in the color liquid 31. Moving brush 111 from the insical to body direction makes it possible to apply more of the first liquid in the top portion of incisal and less of the first liquid in the lower portion of the incisal area, allowing a smooth color transition from the incisal area to the body area of a tooth. After being removed from the second liquid 31, the prosthesis 26 is dried under a light and sintered in a regular way. Then the sintered body displays an ideal multiple color intensity effect with less color/chroma (with optional incisal gray effect with manganese chloride) in the incisal area and more color in the body and cervical area. There is a gradual transition area between incisal and body of a sintered prosthesis. The effectiveness of this coloring method of creating gradually decreasing color intensity/chroma towards the incisal area of a dental prosthesis can be increased when used with a multi-layer zirconia body that has increasing translucency towards the incisal area of a dental prosthesis.

In accordance with another aspect of the present invention, a larger size of blank (typically a round disc) of non pre-colored ceramic material can be more efficient in that the operator can mill multiple teeth all at the same time from the same un-colored discsregardless of individual characteristic requirements and do the coloring job at a separate stage later.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A dental block device for producing a dental prosthesis, the dental block device comprising:
    a) a green body comprising zirconia;
    b) the green body having multiple different layers each having a different chemical composition between adjacent layers;
    c) the different chemical composition including different amounts of yttria between the adjacent layers;
    d) the green body being substantially opaque with a substantially consistent optical characteristic of non-translucency with respect to visible light across the layers;
    e) the green body having a brightness/lightness L* value between 10 to 20 for a sample thickness of 1 to 1.3 mm in accordance with CIE L*a*b* colorimetric system; and
    f) the green body being subsequently millable and sinterable to form the dental prosthesis with the multiple different layers having different optical characteristics of translucency.

2. A device in accordance with claim 1, wherein the amount of yttria is increased incrementally from a lower layer to an upper layer.

3. A device in accordance with claim 2, wherein the amount of yttria is increased incrementally from 4.5-6 wt % in the lower layer to 6-10 wt % in the upper layer.

4. A device in accordance with claim 1, wherein the multiple different layers have different thicknesses with respect to one another with a lower layer having a thickness between 2-5 mm and an upper layer having a thickness between 0.5-2 mm.

5. A device in accordance with claim 1, wherein the green body is without color pigment.

6. A dental block device for producing a dental prosthesis, the dental block device comprising:
   a) a green body comprising 60-99.9 wt % zirconia that is soft sintered or pre-sintered without color pigment;
   b) the green body having a different chemical composition through a thickness of the green body and being substantially opaque with a substantially consistent optical characteristic of non-translucency with respect to visible light through the thickness;
   c) the different chemical composition including increasing amounts of yttria through the thickness with a lower portion having 4.5-6 wt % yttria and an upper portion having 6-10 wt % yttria;
   d) the green body having a brightness/lightness $L^*$ value between 10 to 20 for a sample thickness of 1 to 1.3 mm in accordance with CIE $L^*a^*b^*$ colorimetric system; and
   e) the green body being subsequently millable, colorable and sinterable to form the dental prosthesis with an optical characteristic of increasing translucency through a thickness of the dental prosthesis.

7. A device in accordance with claim 6, wherein the green body is millable to form a green dental prosthesis that is colorable and sinterable to form the dental prosthesis with the optical characteristic of increasing translucency through the thickness of the dental prosthesis after sintering.

8. A device in accordance with claim 6, wherein the green body has multiple different layers with different thicknesses with respect to one another with a lower layer having a thickness between 2-5 mm and an upper layer having a thickness between 0.5-2 mm.

9. A device in accordance with claim 6, wherein the green body has a continuous change in the amount of yttria through the thickness.

* * * * *